US011517694B1

(12) United States Patent
Beaver et al.

(10) Patent No.: US 11,517,694 B1
(45) Date of Patent: Dec. 6, 2022

(54) YANKAUER SUCTION DEVICE WITH AUXILIARY ACCESS PORT

(71) Applicants: Jeremy Joseph Beaver, Millington, TN (US); Vernon Bradley Taylor, Atoka, TN (US)

(72) Inventors: Jeremy Joseph Beaver, Millington, TN (US); Vernon Bradley Taylor, Atoka, TN (US)

(*) Notice: Subject to any disclaimer, the term of this patent is extended or adjusted under 35 U.S.C. 154(b) by 0 days.

(21) Appl. No.: 17/337,897

(22) Filed: Jun. 3, 2021

Related U.S. Application Data

(63) Continuation-in-part of application No. 16/432,778, filed on Jun. 5, 2019, now Pat. No. 11,273,247.

(60) Provisional application No. 62/704,948, filed on Jun. 3, 2019, provisional application No. 62/680,645, filed on Jun. 5, 2018.

(51) Int. Cl.
*A61M 16/04* (2006.01)
*A61M 1/00* (2006.01)
*A61B 17/24* (2006.01)
*A61B 17/50* (2006.01)

(52) U.S. Cl.
CPC .......... *A61M 16/0463* (2013.01); *A61M 1/85* (2021.05); *A61M 16/0409* (2014.02); *A61M 16/0475* (2014.02); *A61B 17/24* (2013.01); *A61B 17/50* (2013.01); *A61M 2202/0208* (2013.01)

(58) Field of Classification Search
CPC . A61M 1/85; A61M 2202/0208; A61B 17/24; A61B 17/50; A61B 10/0233–0283
See application file for complete search history.

(56) References Cited

U.S. PATENT DOCUMENTS

| | | | |
|---|---|---|---|
| 5,538,008 A * | 7/1996 | Crowe | A61B 10/06 606/205 |
| 6,110,127 A | 8/2000 | Suzuki | |
| 8,663,099 B2 | 3/2014 | Tydlaska et al. | |
| 9,386,915 B2 | 7/2016 | Vasan | |
| 10,188,279 B2 | 1/2019 | Vasan | |
| 2003/0176880 A1* | 9/2003 | Long | A61B 10/04 606/205 |
| 2011/0106073 A1 | 5/2011 | Mueller | |
| 2011/0160662 A1* | 6/2011 | Stout | A61M 25/0097 604/122 |

(Continued)

*Primary Examiner* — Thomas McEvoy
(74) *Attorney, Agent, or Firm* — Haynes and Boone, LLP

(57) ABSTRACT

Aspects are directed to an improved suction catheter that increases the effectiveness of clearing the airway, reducing the need for separate suctioning and foreign body grasping instruments. The embodiments described herein provide medical personnel the ability to use one hand and catheter to selectively grasp an anatomically lodged foreign body while reducing the likelihood of lumen blockage and interruption of suction. The embodiments described herein further provide an auxiliary access port that allows insertion of a bougie instrument into a suction catheter. The suction catheter may be a Yankauer device or improved suction catheter with grasping housing. The bougie instrument may extend through the access port and a lumen of the catheter while still providing suction via the lumen. Due to the small size of the suction catheter, the bougie instrument may extend from the catheter's distal end when placed in close proximity to a patient's vocal cords.

13 Claims, 13 Drawing Sheets

(56) References Cited

U.S. PATENT DOCUMENTS

2017/0007792 A1 1/2017 Nye

* cited by examiner

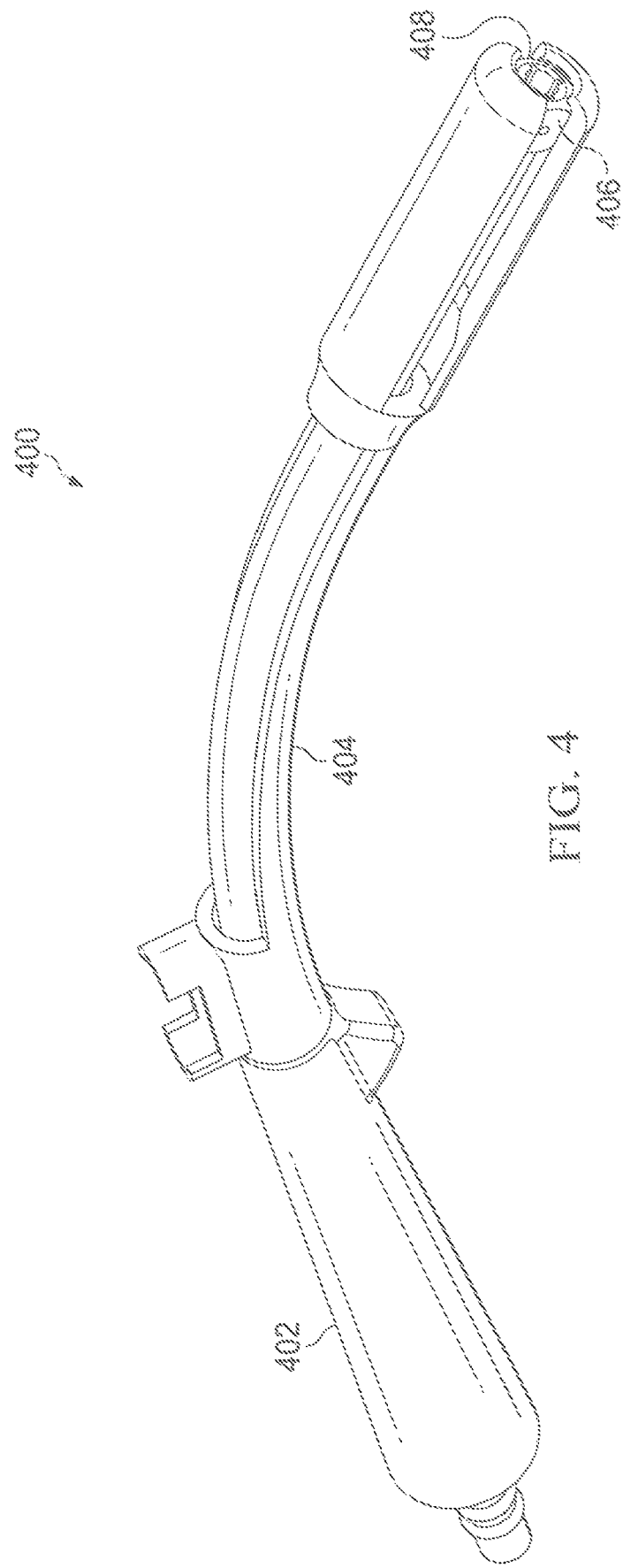

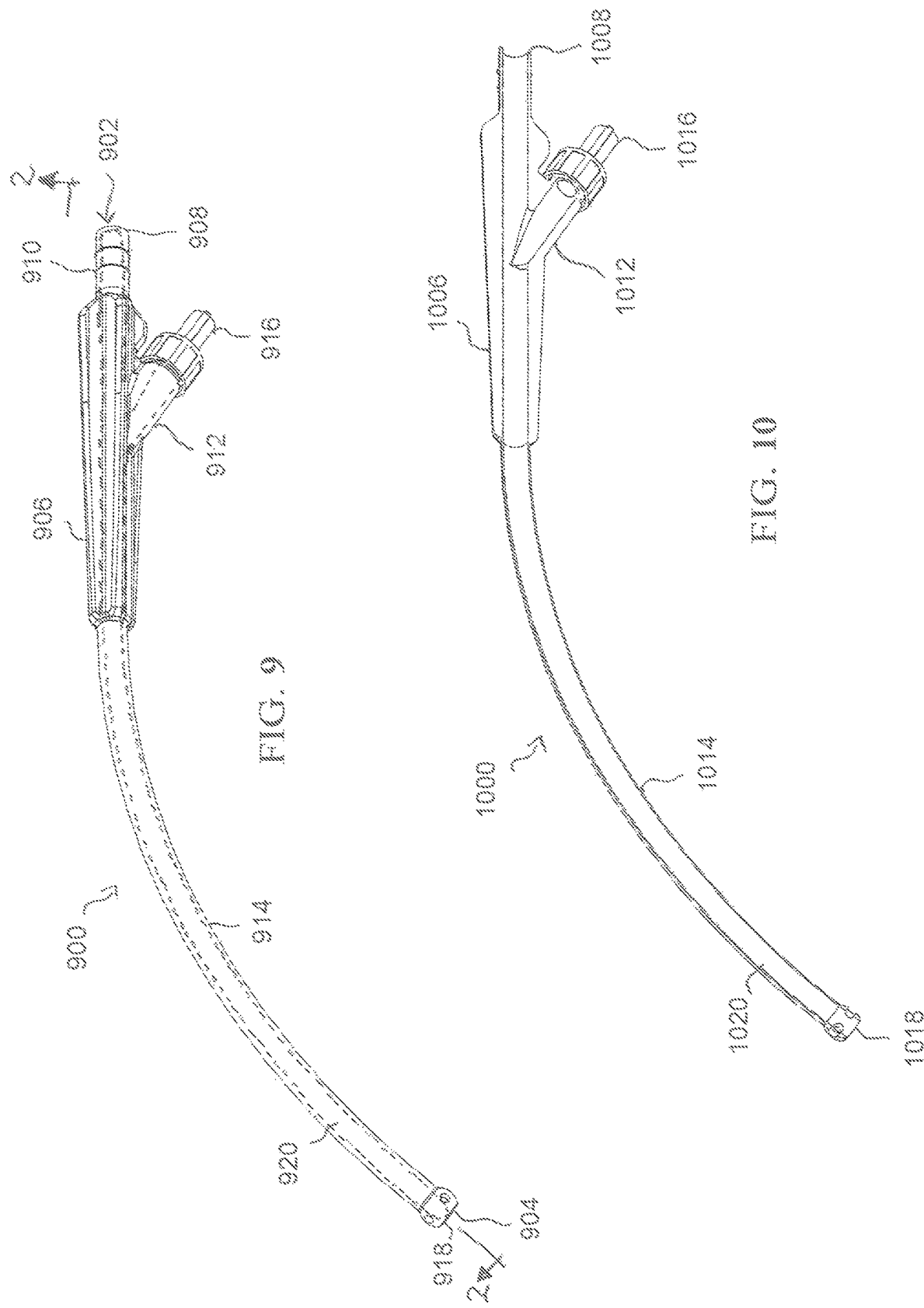

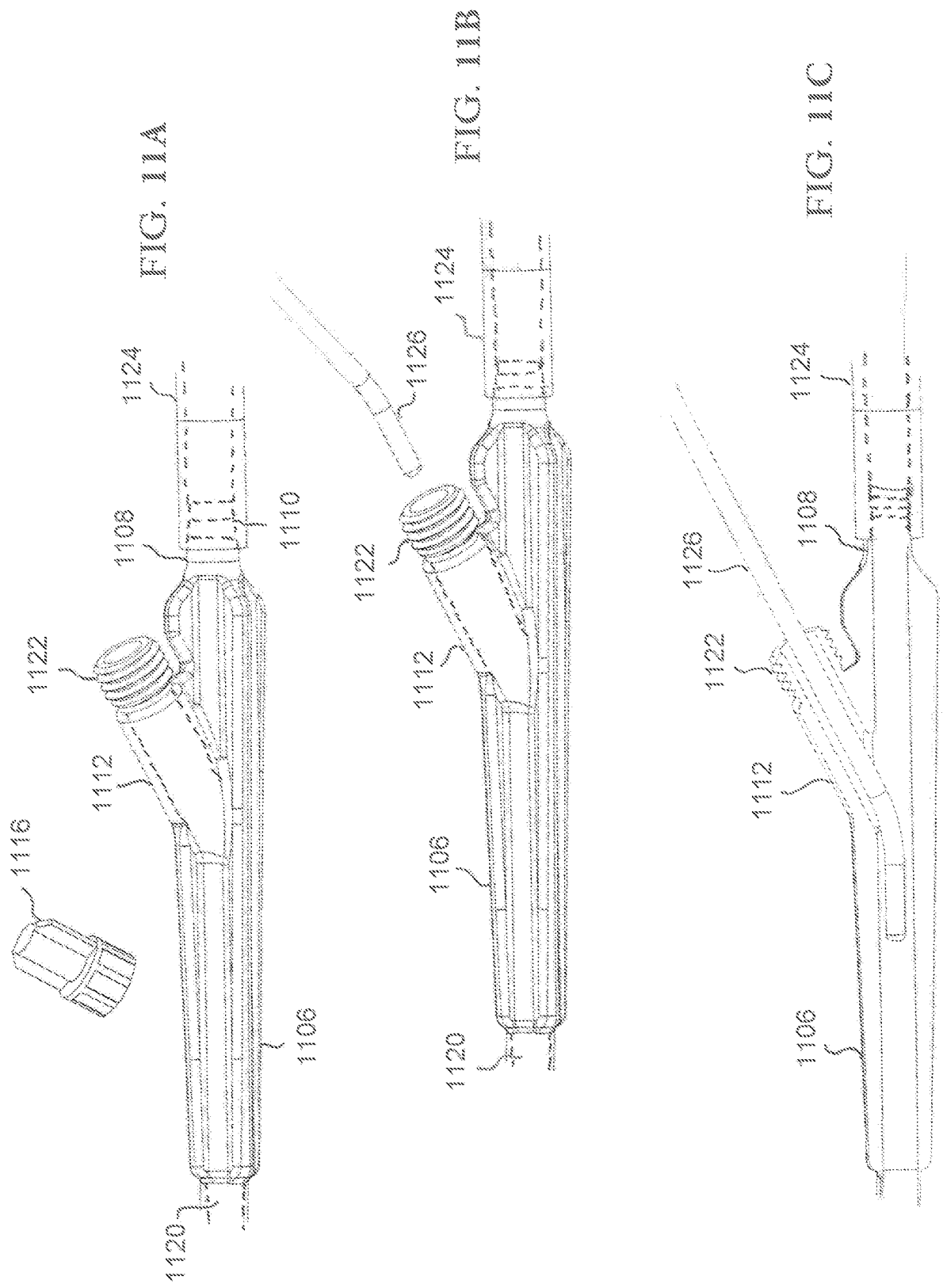

YANKAUER SUCTION DEVICE WITH AUXILIARY ACCESS PORT

CROSS-REFERENCE TO RELATED APPLICATIONS

The present application is a continuation-in-part of U.S. application Ser. No. 16/432,778, filed Jun. 5, 2019, which claims priority to and the benefit of U.S. Provisional Patent Application No. 62/680,645, filed Jun. 5, 2018. The present application also claims priority to and the benefit of U.S. Provisional Patent Application No. 62/704,948, filed Jun. 3, 2020. The disclosure of each application is incorporated by reference herein in its entirety as if fully set forth below in its entirety and for all applicable purposes.

INTRODUCTION

The present invention is in the technical field of airway management. More particularly, in some particular implementations, this invention relates to an improved oropharyngeal device that can be used to suction viscous fluids and selectively grasp and remove foreign bodies, as well as an improved oropharyngeal suction device and method that allow introduction of a bougie instrument through the suction device.

It is a known practice of emergency and medical personnel to use instruments and suction catheters to clear the mouth and oropharyngeal cavity (airway) of gastric contents and body fluids (viscous fluids). The proximal and distal ends of these devices are connected by a conduit capable of transporting fluids when the proximal end is connected by a vacuum hose to a negative pressure device. It is also a known practice of emergency and medical personnel (medical personnel) to use non-suctioning, anatomically contoured instruments such as Magill forceps to grasp items that cannot be efficiently suctioned or scooped including dental fragments, large food particles, chewing gum, and coins (foreign bodies). When clearing the airway, the primary objective of Magill forceps is to precisely grasp and remove foreign bodies while suction of the oropharyngeal cavity is maintained by use of the suction catheter. Medical personnel prefer expeditious evacuation of the airway to return unobstructed breathing to the patient and prevent aspiration of viscous fluids and foreign bodies (unwanted matter). The precise use of separate suctioning and grasping catheters also restrict the use of one hand of attending medical personnel in an emergency situation. In addition, medical personnel must pay special visual attention to the anatomical structures of the airway since they limit both the size and movement of catheters used for the removal of unwanted matter. This restriction of anatomical space is further exacerbated when additional instruments such as laryngoscopes are used for visualization of anatomy and potential foreign bodies.

Known suction catheters are adapted for insertion into the oropharyngeal cavity of a patient and are inefficient at precisely grasping and removing anatomically lodged foreign bodies while maintaining suction. Often, when low viscous fluids and foreign bodies are encountered, blockage of the suctioning device frequently ensues, and removal of the catheter is necessary. When this occurs, medical personnel must momentarily take their eyes off the patient, use at least one hand to clear the obstruction or obtain a replacement device, and reintroduce a working catheter into the airway. In emergency situations, the additional time needed to restart the process of removing unwanted matter can jeopardize the health or life of the patient. To prevent this situation, larger lumen suctioning catheters have been used to help prevent blockage of the catheter but use of excessive suction to dispel debris in close proximity to delicate tissue may result in additional trauma to the fragile structures of the airway. Moreover, suction devices with spoon shaped tips do not offer sufficient rotational mobility of the catheter without spilling the unwanted matter residing within the scoop portion of the spoon.

There are currently no devices that allow medical personnel to optionally add a grasping and removal feature to existing inexpensive suction instruments or catheters. It is also desirable for suction catheters to grasp and remove unwanted matter in the presence of insufficient, intermittent, or absence of vacuum. While prior apparatuses like those disclosed in U.S. Pat. Nos. 7,938,794 and 5,665,080 provide suction and potential for debris removal, there remains a need for suction catheters to be able to provide suction in the presence of blockage of the lumen. The device described herein overcomes one or more deficiencies of the prior art.

BRIEF SUMMARY OF SOME EXAMPLES

The inventive subject matter includes: a suction catheter of a size suitable for insertion into a body cavity made of an elongated suction tube formed of a polycarbonate, acrylic, plastic, or suitable material having a lumen running interiorly thereof, the tube having an distal suction tip with an opening for placing the lumen in communication with the interior of the body cavity and a proximal end adapted to place the lumen in communication with a source of pressure lower than that existing at the distal end of the tube, wherein the improvement includes: a slidably disposed grasping housing affixed to the outside of the catheter. More specifically, the present invention provides a suction catheter with a slidably disposed grasping housing affixed to the outside of the catheter and used by medical personnel to facilitate selective grasping and removal of unwanted matter within the airway.

In one aspect, the device is made of a substantially hollow suctioning tube coupled to an elongated grip or handle. The device is attached to a suction hose and negative pressure device well known within the art and capable of transporting unwanted matter from the distal end of the device through the proximal end of the handle. In another aspect, the distal end of elongated grip or handle may contain an integrated finger rest to increase ergonomics and provide greater operational control of the device. The proximal end of the handle comprises a vacuum attachment port with compression rings configured to receive and seal to the interior of a vacuum hose.

In yet another aspect, the distal end of the elongated suction tube includes a suction tip that has an auxiliary suction channels longitudinally extending with and in fluid communication to the interior lumen of the device to facilitate continued removal of viscous fluids in the event of blockage of the lumen. In yet a further aspect of the device, the distal end of the suctioning tube terminates into a radiused tip with radiused top and bottom portions separated by reduced radius lateral sides which allow better anatomical visualization by medical personnel. In another aspect, the lateral sides of the suction tip may contain at least one optional orifice that is in fluid communication with the lumen and allows lateral vacuuming and removal of unwanted matter.

In an embodiment, the suction catheter assembly includes a slidably disposed grasping housing adapted to attach to the outside of catheter. The inside of the grasping housing contains at least one radius and is configured to receive the elongated suction tube and suction tip of the suction catheter. The proximal and distal ends of the grasping housing may open and close, with the left side having a male locking element and a right side having a female locking element, wherein the interface of the male and female elements lock and secure the grasping housing to the suction catheter when downward compression is applied to the interface of the locking elements. However, it will be appreciated that the proximal and distal segments of the grasping housing may be optionally or permanently attached to the suction catheter device by other means including gluing, bonding, compression fitting, or thermal securement. Moreover, the slidably disposed grasping housing may be sufficiently flexible to accommodate the existing curvatures of other suction catheters.

In one embodiment, a thumb rest is located on the top portion of the proximal end of the grasping housing. The distal end of the grasping housing contains a plurality of at least two grasping arms which are configured to curve around the perimeter of the radiused sections of the suction tip and extend to the inside radius of the lumen.

In another embodiment, the inside radius of the terminating ends of the grasping arms are configured to serve as grasping tips for the removal of foreign bodies and unwanted debris. It is appreciated that the terminating ends of the grasping tips may be blunt, sharp, serrated, or otherwise configured to grasp and retrieve a foreign body.

In yet another embodiment, opening and closing of the grasping arms and grasping tips are activated by extension and retraction displacement of the thumb rest located on the top of the proximal end of grasping housing. As the grasping housing is advanced distally away from the proximal end of the handle, movement of the suction tip within the inside taper of the diametrically opposed grasping arms forces the grasping tips to expand. The expansion of the grasping tips facilitates grasping and removal of a foreign body. Further distal advancement of the grasping housing causes the suction tip to engage a chamfer connected to a recess towards the proximal end of medial walls of the grasping arms. The recess within the medial walls of the grasping arms is configured to receive the suction tip. Entry of the suction tip into the recess allows the grasping arms and grasping tips to retract from their expanded state and engage a foreign body. Furthermore, the grasping tips may be expanded and retracted to engage a foreign body in the absence or presence of suction through the Suction device. Medical personnel may optionally retain the foreign body in the grasping tips and continue suction while the foreign body is displaced a distance away from the suction tip or continue suction and removal of unwanted matter through the lumen while the foreign body is retracted closer to the suction tip. At the discretion of the medical personnel, the grasping housing may be fully retracted for removal of the foreign body from the grasping tips.

The inventive subject matter further includes a catheter device of a size suitable for insertion into a body cavity comprising an elongated suction tube having a lumen running interiorly thereof, wherein the elongated suction tube is of a shaped to accommodate clearance of foreign bodies, the tube having an distal suction tip with an opening for placing the lumen in communication with the interior of the body cavity and a proximal end adapted to place the lumen in communication with a source of pressure lower than that existing at the distal end of the tube within a grasping housing, the distal end of the elongated suction tube made of an at least two sets of pegs; a grasping housing slidably disposed around at least a portion of the elongated suction tube and the distal suction tip, wherein the grasping housing is comprised of an at least one radius and the radius is configured to receive the elongated suction tube and distal suction tip of the suction catheter, wherein the grasping housing is made of an upper grasping arm and a lower grasping arm, wherein the at least two sets of pegs of the elongated suction tube are configured to engage with a plurality of slot ramps on the grasping arms.

The inventive subject matter further includes a method to selectively grasp and remove unwanted matter during a medical procedure on a patient involving suction, using a single instrument by providing the steps of: inserting a suction catheter into the airway or cavity of a patient; wherein the suction catheter is made of: an elongated suction tube having a lumen running interiorly thereof, the tube having an distal suction tip with an opening for placing the lumen in communication with the interior of the body cavity and a proximal end adapted to place the lumen in communication with a source of pressure lower than that existing at the distal end of the tube within a housing, a grasping housing slidably disposed around at least a portion of the elongated suction tube and the distal suction tip, wherein the grasping housing is made of at least one radius and the radius is configured to receive the elongated suction tube and distal suction tip of the suction catheter, wherein the distal end of the grasping housing is comprised of a plurality of at least two grasping arms which are configured to curve around the suction tip and mate to the outside radius of the lumen and wherein each of the at least two grasping arms terminated in a grasping tip; moving the grasping housing distally along an elongated suction tube whereby the two grasping arm sections grasp the unwanted matter; and retracting the grasping housing to remove the object, while providing suction through the elongated suction tube.

These and other aspects, embodiments, features, and advantages of the invention shall become fully apparent from the following detailed descriptions and accompanying drawings.

BRIEF DESCRIPTION OF THE DRAWINGS

FIG. 4 illustrates a right front perspective view of the device of FIG. 1.

FIG. 9 illustrates a left front perspective view of a Yankauer suction device with an auxiliary access port of the present invention.

FIG. 10 illustrates a sectional view taken about lines 2-2 of FIG. 9.

FIGS. 11(A)-11(D) illustrate four sequential operational views of the auxiliary access port of the Yankauer device of FIG. 9.

DETAILED DESCRIPTION

Figure 1:
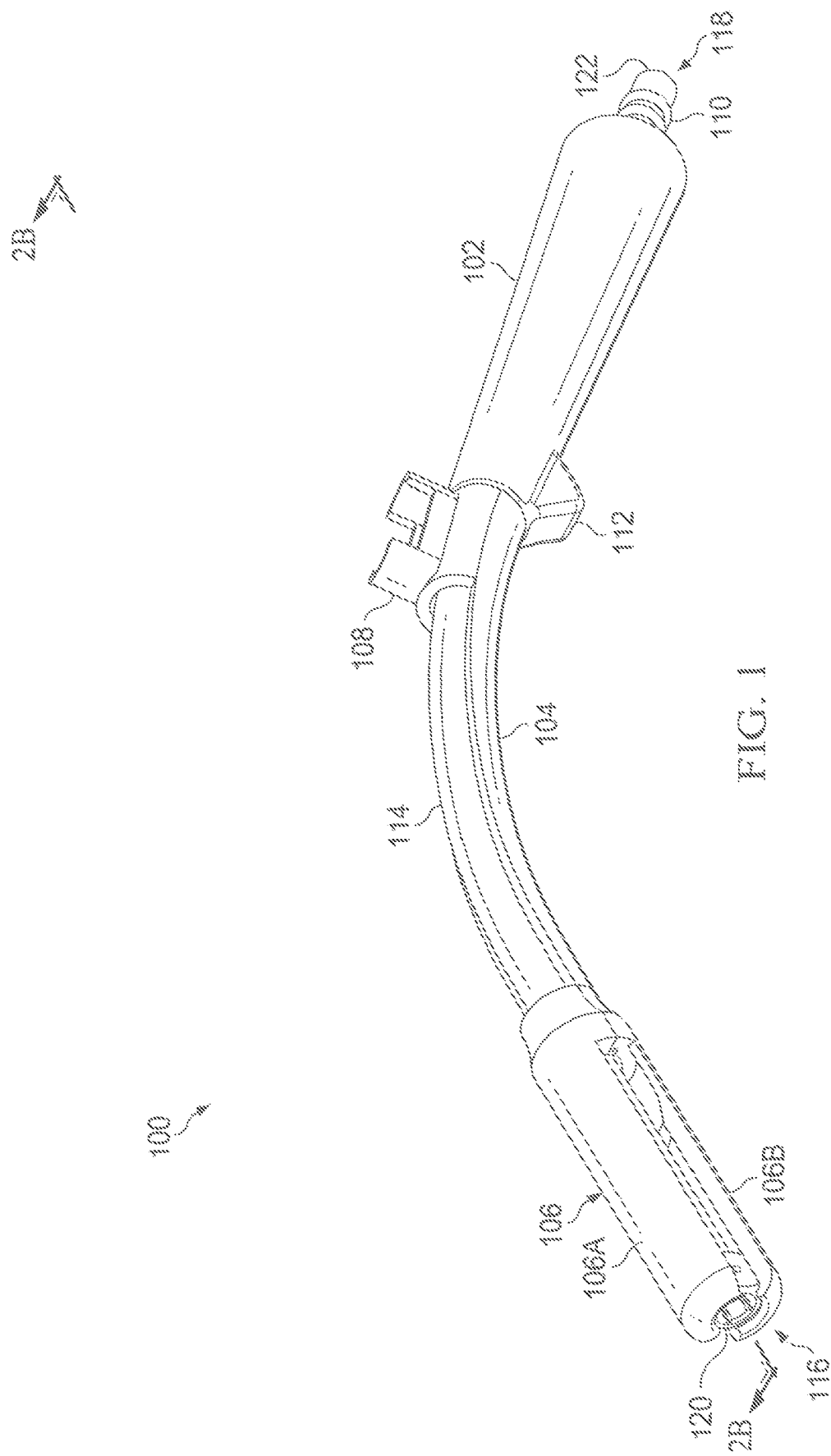
FIG. 1 illustrates a left front perspective view of the device of the present invention.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details.

Any alterations and further modifications to the described devices, and any further application of the principles of the present invention are fully contemplated as would normally occur to one skilled in the art to which the disclosure relates. In particular, it is fully contemplated that the features and components described with respect to one embodiment may be combined with the features and components described with respect to other embodiments of the present invention. In addition, dimensions provided herein are for specific examples and it is contemplated that different sizes, dimensions, and/or ratios may be utilized to implement the concepts of the present invention. To avoid needless descriptive repetition, one or more components or actions described in accordance with one illustrative embodiment can be used or omitted as applicable from other illustrative embodiments.

For the purpose of clarification and described herein, suction instrument and suction catheter may be used interchangeably and are defined as oral or other cavity suctioning catheters designed to be used by medical personnel in the oropharyngeal cavity. Moreover, mouth, airway, and oropharyngeal cavity may be used interchangeably and are defined as anatomical cavities and structures between the inferior aspect of the soft and hard palates and extending to the superior aspect of the vocal cords.

The present invention is directed to an oropharyngeal device for improved airway management by adding a slidably disposed grasping housing to the outside of a suction catheter. The improved suction catheter increases the effectiveness of clearing the airway by way of non-limiting example, reducing the need for separate suctioning and foreign body grasping instruments. For example, grasping a foreign body beyond contact with the suction tip reduces the chance of blockage of the lumen and interruption of suction. Moreover, auxiliary suction channels may help evacuate viscous fluids in the event of interruption of suction. In some instances, grasping foreign bodies beyond the tip of the suction device diminishes the likelihood of causing additional airway trauma by the suction tip. The embodiments described herein provide medical personnel the ability to use one hand and catheter to selectively grasp an anatomically lodged foreign body while reducing the likelihood of lumen blockage and interruption of suction.

In addition, some embodiments may add the ability to grasp and remove foreign bodies to existing suction catheter or instruments, thereby reducing the limitations of these inexpensive devices. In some instances, using one hand to grasp foreign bodies and evacuate the airway reduces procedure time and permits medical personnel use of their free hand to maintain control of laryngoscopes or other catheteration. The airway management device disclosed herein can optionally, cost-effectively, efficiently, and safely grasp and remove a foreign body while reducing the occurrence of interruption of suction.

Turning now to FIG. 1, the preferred embodiment of the present invention, there is shown a suction catheter device 100 constructed in accordance with the principles of the present invention. As is illustrated in the front perspective view of FIG. 1, the catheter device 100 has a proximal end 118 and a distal end 116. A handle section 102 has an elongated handle with a hollow suction port 122 at its distal end. The exterior of the suction port 122 has a set of compression fitting rings 110 configured to attach to a vacuum hose and negative pressure source. A finger rest 112 is integrated posteriorly into the distal end of the handle 102. A hollow elongated suction tube 114 extends from the distal end of the handle 102 and terminates into a suction tip 120.

The catheter device 100 includes a movably connected grasping housing 104. The grasping housing 104 can for integrally formed with the catheter device 100 or be a separate attachable unit that can be removably attached. The grasping housing 104 extends proximally to the distal end of the handle and distally to the outside of the suction tip 120. The grasping housing 104 is configured to receive both the elongated suction tube 114 and suction tip 120 and is proximally attached to the elongated suction tube 114 by a thumb rest collar 108. The thumb rest collar 108 has opposing lateral sides, approximately the width of the suction tube 114, with raised proximal and distal ends configured to receive the thumb of medical personnel. The grasping housing 104 is attached distally to the elongated suction tube 114 by a grasping arm collar 106. The grasping arm collar 106 is composed of an upper grasping arm 106A and a lower grasping arm 106B.

Figure 2A:
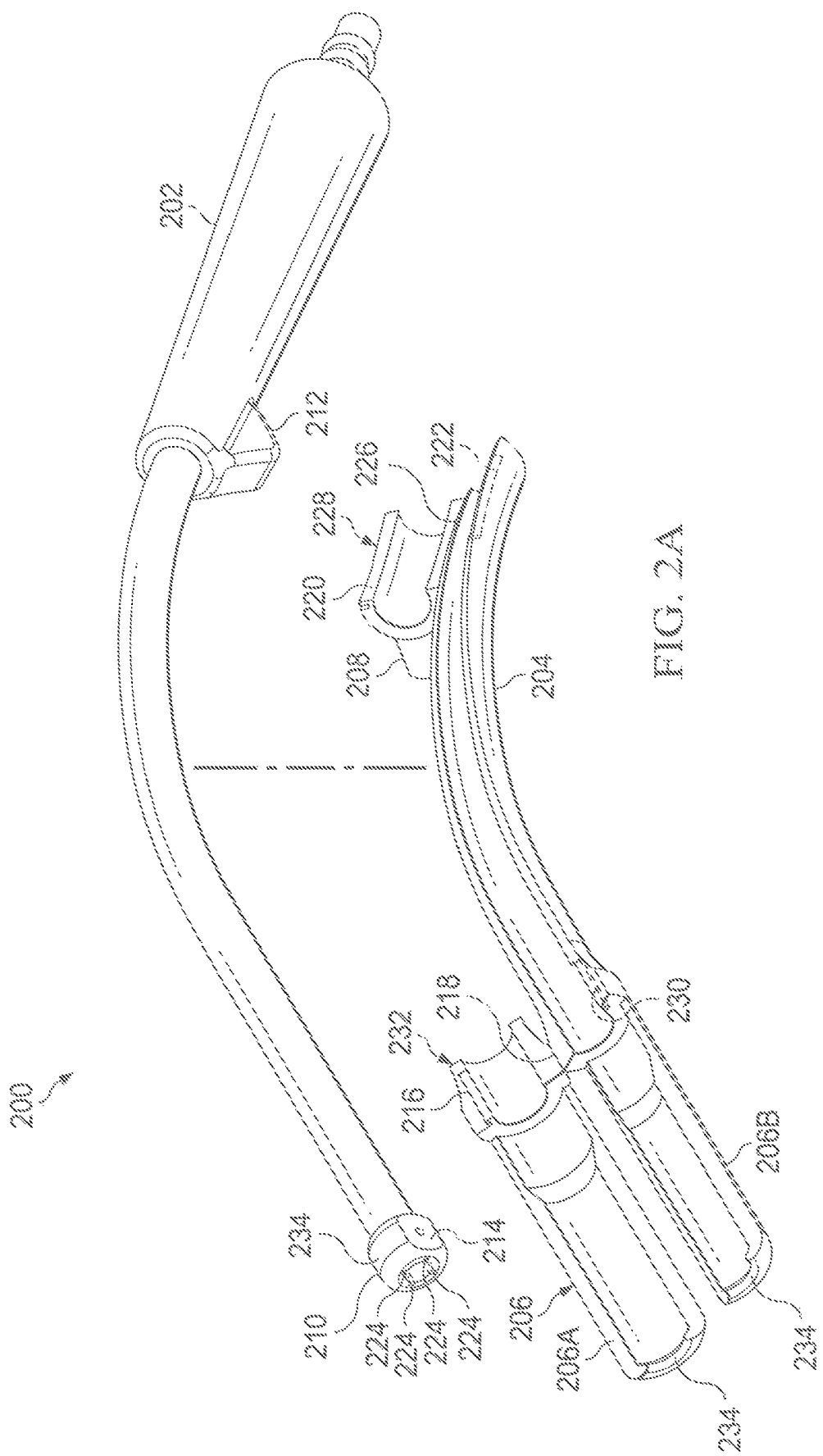
FIG. 2A illustrates a front perspective exploded view of the device of FIG. 1.
Figure 2B:
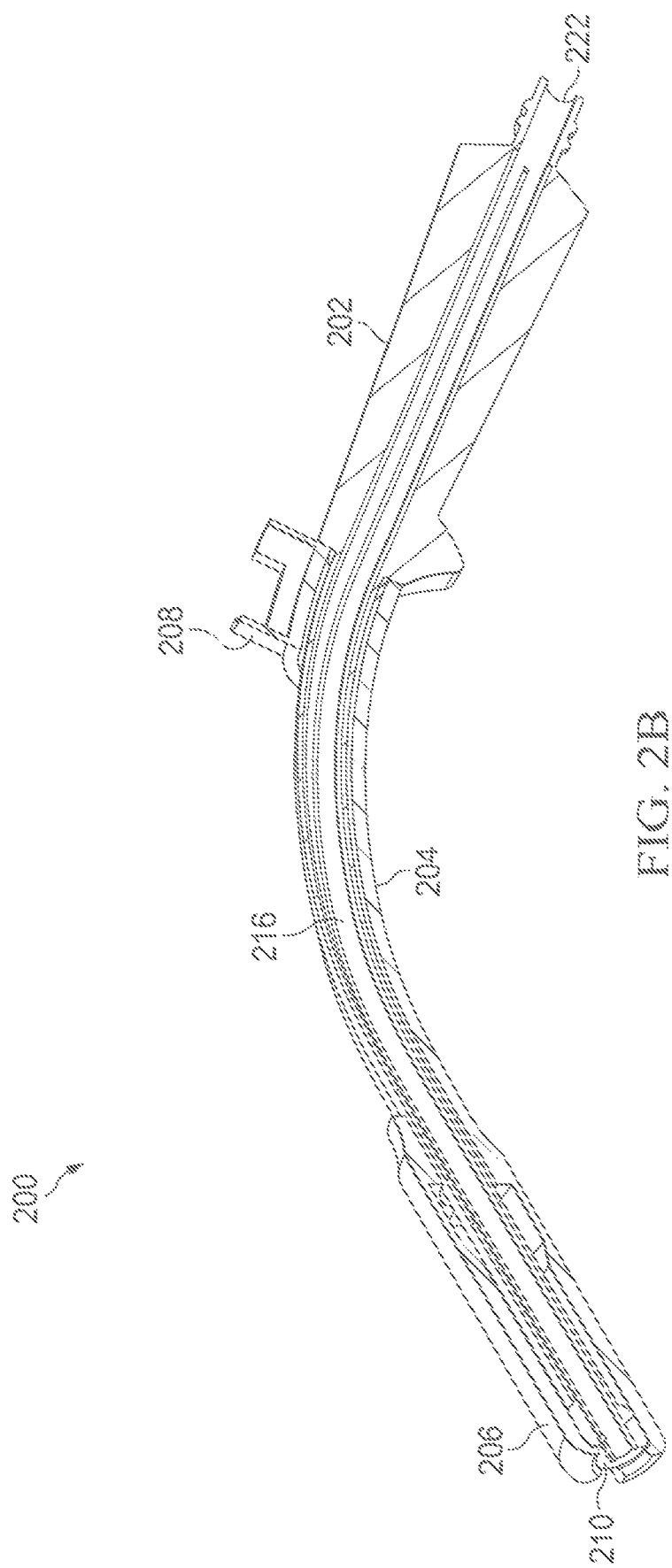
FIG. 2B illustrates a sectional view taken about lines 2B-2B of FIG. 1.

As is more clearly illustrated in FIGS. 2A-2B, the front perspective exploded view best illustrates a suction tip 210 and the attachment of a grasping housing 204 to a catheter device 200. A thumb rest collar 228 is flexibly attached to the proximal end of a grasping housing 204 by an integrated hinge 226. Moreover, the thumb rest collar 228 contains a concave anterior wall with a radius configured to receive the catheter device 200. The terminating side of the thumb rest housing 220 has a male locking element that locks into a female locking element 222 of the grasping housing 204 when the thumb rest housing 220 is rotated and closed by compression. The slidable grasping housing 204, which further includes thumb rest collar 208 and grasping arms 206, is moved back and forth along hollow elongated suction tube 214 by means of the thumb rest collar 208.

Located distally of the grasping housing 204 is a grasping arm collar 232 flexibly attached by an integrated hinge 218 to the grasping housing 204. The grasping arm collar 232 contains a concave anterior wall with a radius configured to receive the device 200. A terminating side of the grasping arm collar 216 has a male locking element that locks into a female locking element 230 of grasping housing 204 when the grasping arm collar 232 is rotated and closed by compression.

Referring still to FIG. 2A, in one embodiment and extending distally from the grasping arm collar 232 are a pair of grasping arms 206 made of an anterior grasping arm 206A and a posterior grasping arm 206B. The grasping arms 206A and 206B extend distally around the anterior and posterior segment of a suction tip 210, medially to the lumen radius of the suction tip 210 and terminate into a pair of grasping tips 234.

The suction tip 210 is integrated and attached to the distal end of the device 200 and contains a top and bottom segment that is radiused. At least one lateral side 214 is positioned between the top and bottom segment of the suction tip 210. The lateral side 214 is flat while the top and bottom portions are radiused. For large objects the grasping arms 206 need to be open a large amount, therefore most of the expansion was packaged in the first portion of sliding to minimize "pushing away" of large objects. The range of the opening distance between grasping arms 206 can be from 0.01 mm to 35 mm.

FIG. 2B illustrates a sectional view of another embodiment of the present invention. An auxiliary suction channel 210 is depicted fluidly communicating with a lumen 216 and longitudinally running from the distal end of a device 200 and terminating at the proximal end of a handle 202. The lumen 216 is shown running from the distal end of the device 200 through the proximal end of a suction port 222. The inside lumen of the suction tip 210 has a range in width of 0.1 to 20 millimeters. A plurality of auxiliary suction channels 224 fluidly connect to the lumen of the catheter device 200 and extend longitudinally from the terminating end of the suction tip 210 to the posterior end of the handle 202. Each side of the auxiliary suction channels 224 is approximately 0.5 to 1.5 mm in width. Alternatively, the auxiliary suction channels 224 are approximately one mm$^2$ each.

Figure 3A:
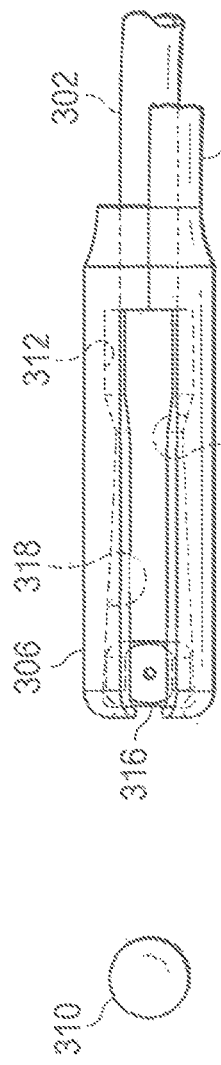
FIGS. 3(A)-3(C) illustrate three partial side views of the distal end of the device of FIG. 1.
Figure 3B:
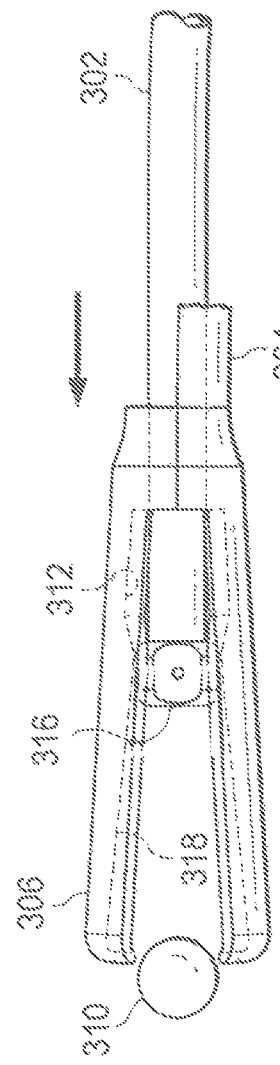
Figure 3C:
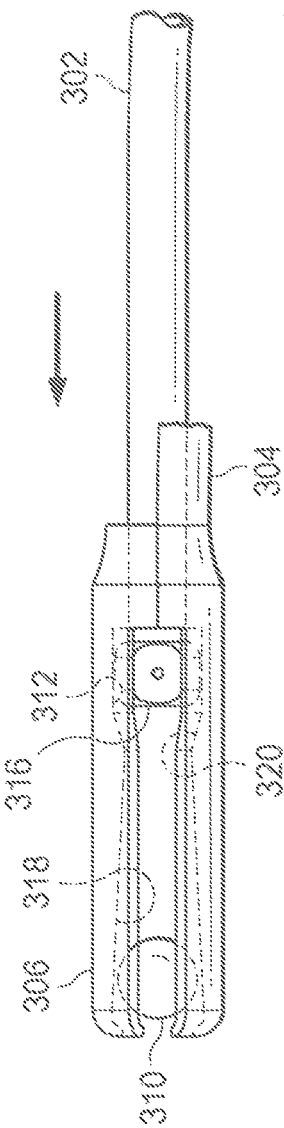

FIGS. 3A, 3B and 3C are partial side views of the present invention that illustrate the movement, position and operation of the grasping arms 306 in relation to a suction tip 316 and an elongated suction tube 302. The suction tip 316 is integrally connected to the distal end of an elongated suction tube 302. The anterior and posterior segments of the suction tip 316 are in contact with the medial sides of a pair of grasping arms 306. Commencing on the posterior side of the grasping tips, each grasping arm 306 has on its medial side a decreasing taper 318 which is distally connected to a chamfer 320. The proximal side of the chamfer 320 is attached to a recess 312 configured to receive the suction tip 316. Collectively, the lengths of the decreasing radius 318, chamfer 320, and recess 312 run approximately the length of the medial sides of the grasping arms 306.

Referring to FIG. 3A, with the grasping arms 306 in a closed (retracted position), the distal end of suction tip 316 contacts the distal end of the grasping arms. Referring now to FIG. 3B, as the grasping housing 304 is extended distally towards a foreign body 310, contact of the anterior and posterior segments of suction tip 316 along the decreasing taper 318 force the grasping arms 306 and grasping tips 322 to expand. Referring now to FIG. 3C, as expanded (opened) grasping arms 306 are positioned to grasp the foreign body 310 and the grasping housing 304 is pushed farther distally, the suction tip 310 enters the chamfer and the grasping arms 306 begin to retract. Upon entry of the suction tip 310 into the recess 312, the grasping arms 306 and grasping tips 322 are fully retracted.

In summary referring to FIGS. 1, 2A, 2B, 3A, 3B and 3C, the suction catheter can be equipped with a slidable grasping housing 204. The slidable grasping housing 204, which further includes thumb rest collar 108 and grasping arms 206, is moved back and forth along hollow elongated suction tube 114 by means of the thumb rest collar 208. The grasping housing 204 along with other elements mentioned in previous paragraph is molded or made in one piece, with both ends in a split half configuration with female locking elements 222 and 230 so that the device can be applied to hollow elongated suction tube 114 by placing it under the hollow elongated suction tube 114, folding the two halves of each end over against each other, and snapping them together with female locking elements 222 and 230.

The grasping housing 204 distal end, when assembled as described above, contains the radiused end of the suction tip 210 within it. When fully snapped together, the gripping device can be moved back and forth along the hollow elongated suction tube 114 which causes the two grasping arm sections 206A and 206B (could be more than two sections) to open or close as the decreasing radius 318, chamfer 320, and recess 312 are forced back and forth over the radiused end of the suction tip 210 by means of the thumb rest collar 208. A finger rest 212 is integrated posteriorly into the distal end of the handle 202.

FIG. 4. is another embodiment illustrating a right front perspective of a device 400. The left lateral side of the suction tip 408 is depicted in this illustration. The grasping housing 404 has a grasping arm collar 406. The device 400 further includes an elongated handle 402.

The preferred dimensions of the suction devices are 20 to 25 cm. in length and the preferably internal diameter of the lumen is two to nine millimeters. Ideally, the inside diameter at the suction tip is smaller than the inside diameter at the proximal end of the handle. Optionally, the inside diameter of the lumen can remain constant. However, the preferences of medical personnel, patient size and circumstance ultimately determine the preferred dimensions of the device.

Figure 5:
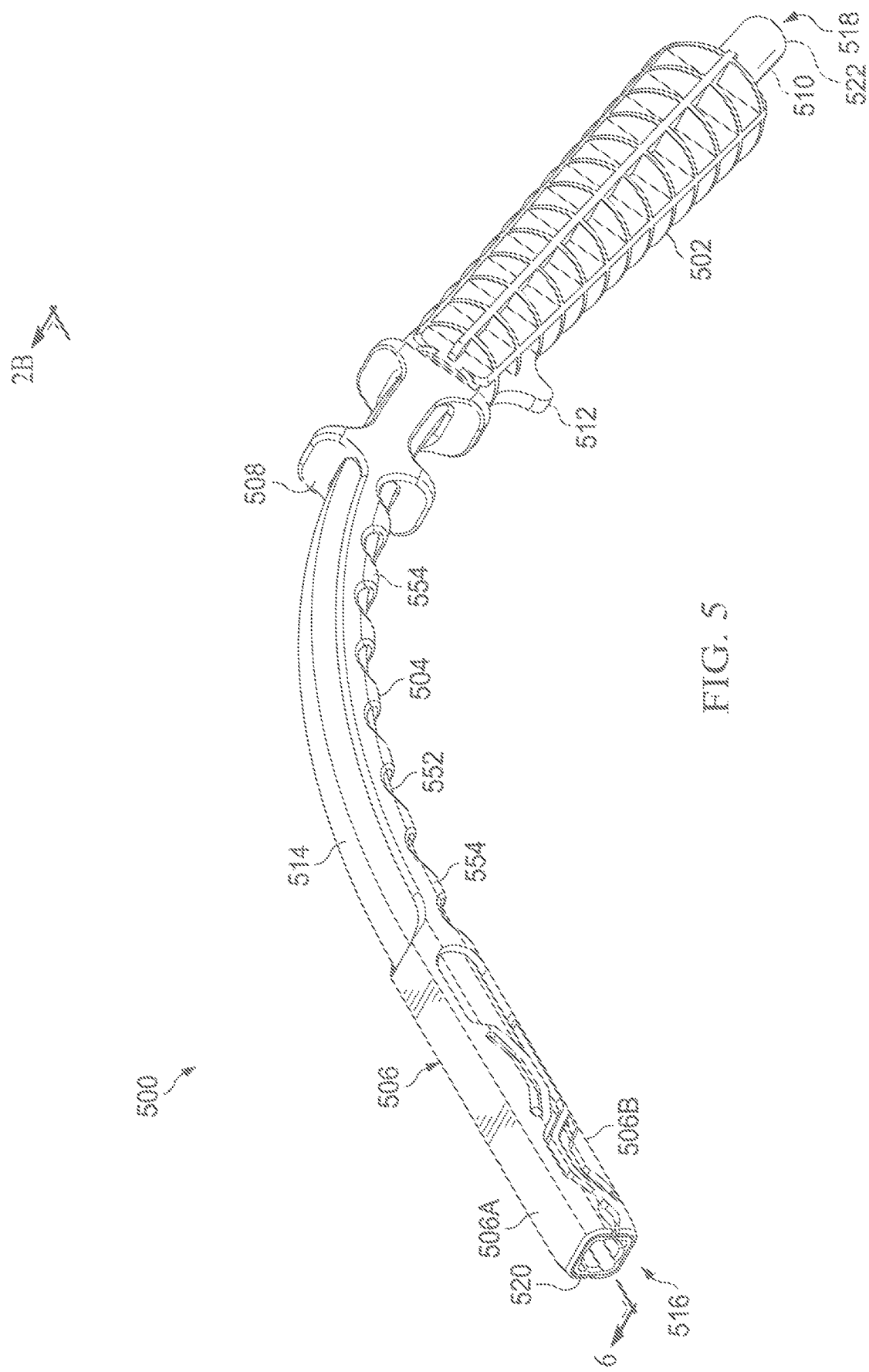
FIG. 5 illustrates a left front perspective view of the device of the present invention.
Figure 6:
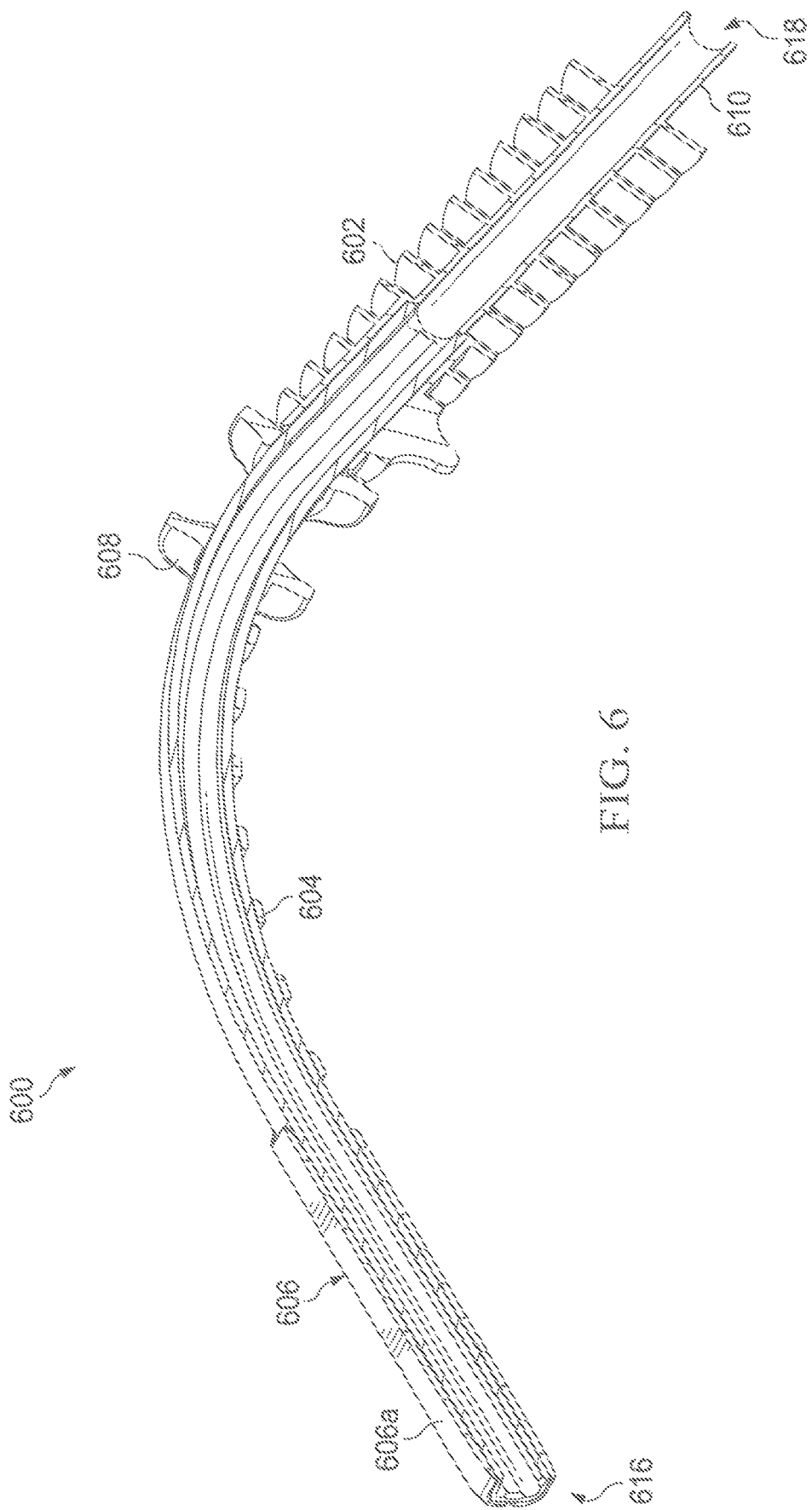
FIG. 6 illustrates a left front perspective view of the device of the present invention.

Now referring to FIGS. 5-6, a catheter device 500, 600 is shown in accordance with the principles of the present invention. The catheter device 500, 600 has a proximal end 518, 618 and a distal end 516, 616. A handle section 502, 602 has an elongated handle with a hollow suction port 522 at its distal end. The exterior of the suction port 522 has a set of compression fitting rings 510, 610 configured to attach to a vacuum hose and negative pressure source. A finger rest 512 is integrated posteriorly into the distal end of the handle 502. A hollow elongated suction tube 514 extends from the distal end of the handle 502 and terminates into a suction tip 520. In an exemplary embodiment, the hollow elongated suction tube 514 is squarely shaped.

Attached to the outside of the device 500, 600 is a movably connected grasping housing 504, 604. The grasping housing 504 extends proximally to the distal end of the handle and distally to the outside of the suction tip 520. The grasping housing 504 is configured to receive both the elongated suction tube 514 and suction tip 520 and is proximally attached to the elongated suction tube 514 by a thumb rest collar 508, 608. The elongated suction tube 514 is made of a curved suction tube of adequate radius to achieve smooth accuation of the grasping arms 506, 606. Additionally, the elongated suction tube 514 is of a shape to accommodate clearance of foreign bodies.

In this embodiment, the grasping housing 504 is configured to receive both the suction tube 514 and suction tip 520 are generally square shaped in an exemplary embodiment. The thumb rest collar 508 has opposing lateral sides, approximately the width of the elongated suction tube 514, with raised proximal and distal ends configured to receive the thumb of medical personnel. The grasping housing 504 is attached distally to the elongated suction tube 514 by a grasping arm collar 506. The grasping arm collar 506 is composed of an upper grasping arm 506A and a lower grasping arm 506B. (upper grasping arm 606a shown in FIG. 6). The grasping housing 504 has an underside 552 with a series of convex rounded projections 554. There projections assist in with the actuation of the grasping housing 504 over the elongated suction tube 514.

Now referring to FIGS. 5 and 7A-7D partial side views of the present invention illustrate the movement, position and operation of the grasping arms 706 in relation to a suction tip 716 and an elongated suction tube 714. The suction tip 716 is integrally connected to the distal end of an elongated suction tube 714. The anterior and posterior segments of the suction tip 716 are in contact with the medial sides of a pair of grasping arms 706. The elongated suction tube 714 has two sets of pegs 770 for engaging with a plurality of slots ramps 780, 781 on the grasping arms 706. More specifically, the top grasping arm 706A has a pair of back slots ramps 780. The bottom grasping arm 706B has a pair of back slots ramps 781. The shape of the ramp portion of the slots dictates the force required to open/close the grasping arms 706 as well as the expansion amount, and can be contoured accordingly to give the motion/force-per-sliding-amount desired.

The grasping housing 704 is retained to the elongated suction tube 714 because the at least two sets of pegs 770 are within closed slots ramps 780, 781. The suction catheter device 500 is assembled by elastically deforming grasping housing 704 slots ramps 780, 781 wider than the at least two sets of pegs 770, then releasing once the pegs 770 are in the slot ramp 780, 781, capturing the pegs 770 grasping housing 704 to the elongated suction tube 714.

Figure 7A:
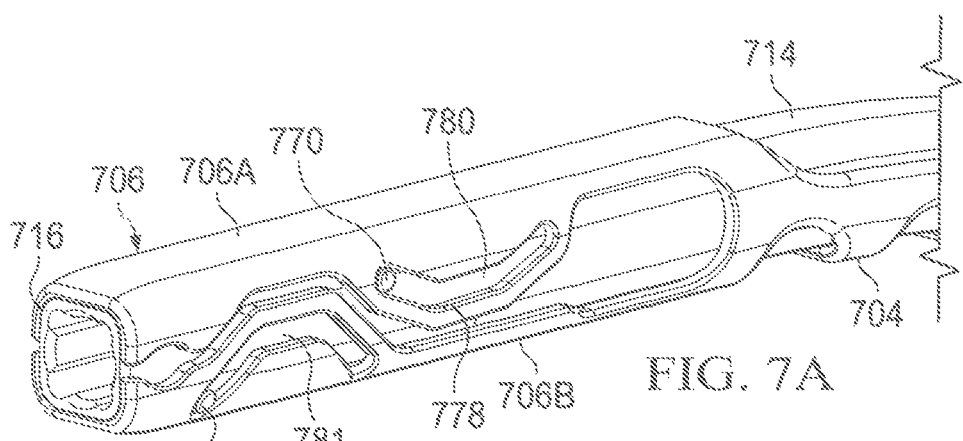
FIGS. 7(A)-7(D) illustrate three partial side views of the distal end of the device of FIG. 5.
Figure 7B:
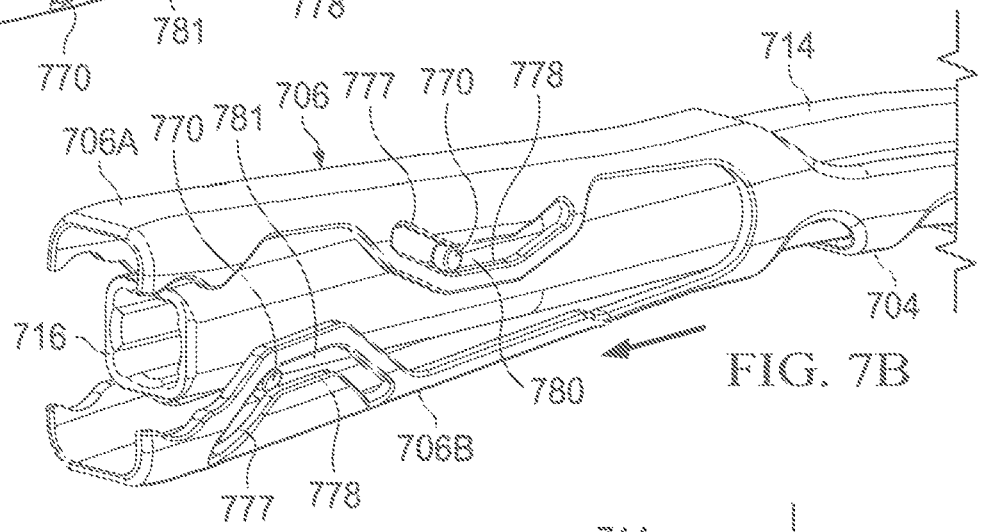

Now referring to FIG. 7B the grasping housing 704 is advanced forward and the grasping arms 706 open. As shown the grasping arms 706 are opened approximately eighty percent when the at least two sets pegs 770 are in the first semi vertical portion 777 of the slot ramps 780, 781.

Figure 7C:
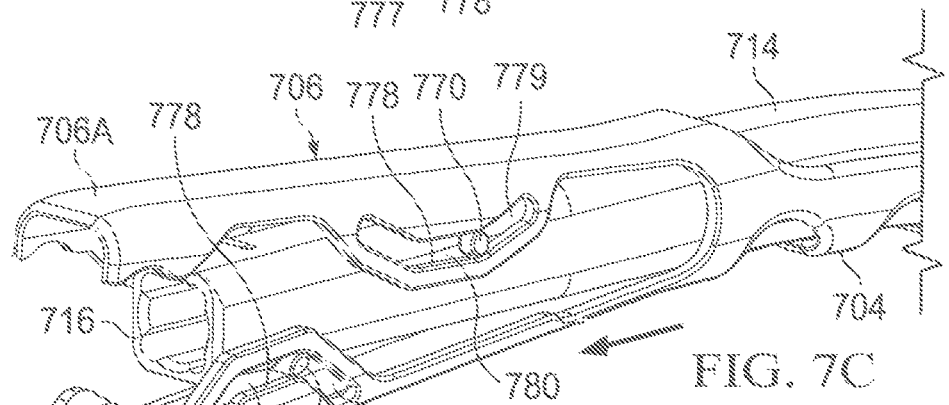

Now referring to FIG. 7C the grasping arms 706 of the grasping housing 704 is advanced forward and the grasping arms 706 open wider. The grasping arms 706 are opened the remaining twenty percent during this portion of the motion, wherein the at least two sets of pegs 770 are in the horizontal portion 778 of the slot ramps 780, 781. Specifically, the full amount of opening could be captured in the first part of the motion if desired. Generally, any XX amount of opening per YY sliding motion could be captured with the ramp/slot shape. In one exemplary embodiment, the width of the gap between grasping arms 706A and grasping arms 706B is 12.5 mm.

Figure 7D:
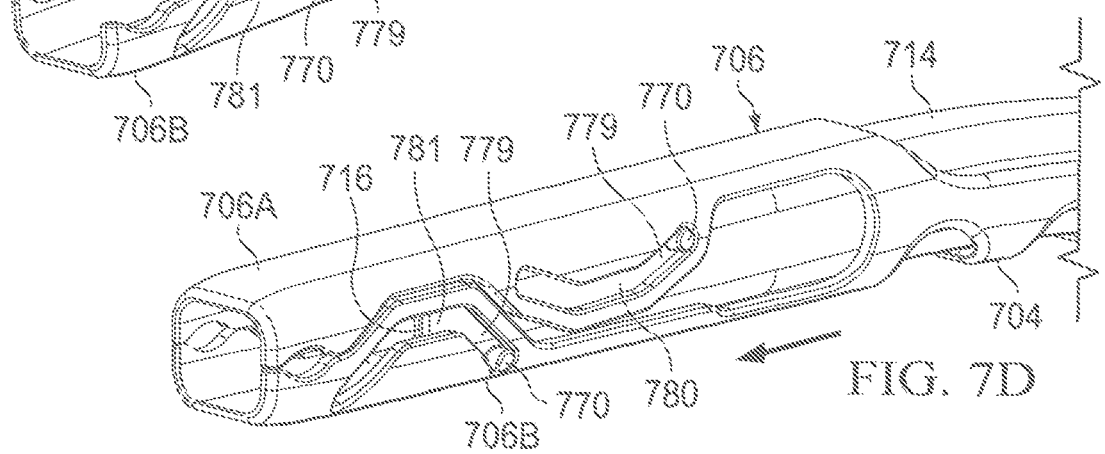

Now referring to FIG. 7D the grasping arms 706 of the grasping housing 704 is advanced forward. The grasping arms 706 are closed when the at least two sets pegs 770 are in the second semi vertical portion 779 of the slot ramps 780, 781.

Figure 8:
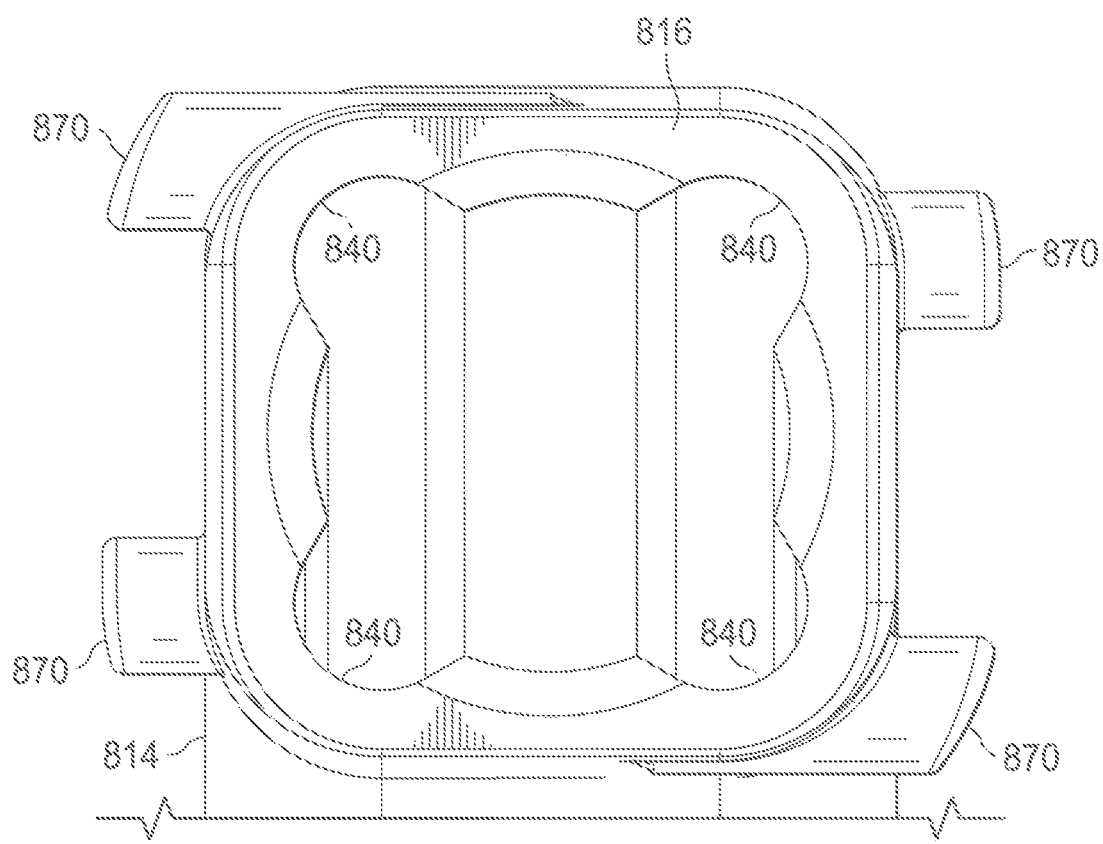
FIG. 8 illustrates a sectional view of the device of FIG. 5.

Now referring to FIG. 8, a cross-sectional view of a catheter device is shown. A main central bore 816 with four lobes 840 at the corners is provided. The two sets of pegs 870 are also shown at the corners and are off set from each other to increase structural strength of the elongated suction tube 814. The four lobes 840 allow transportation of liquid, even if the main bore is blocked with a chunk.

Benefit of this subject matter include: 1) Can force the grasping arms 706 closed in the fully retracted position providing a tight, closed profile, reducing the incidence of catching on surrounding tissue during insertion; 2) Offer prevention of the grasping arms 706 disarticulating with the inner tube during sliding if they encounter surrounding tissue, and; 3) Provide positive grasping force in the fully extended position.

This disclosure describes a novel catheter device which is specifically designed to enter the oropharyngeal cavity and has the benefits of allowing medical personnel the ability to simultaneously evacuate viscous fluids while grasping foreign bodies with a single catheter and one hand. The implementation of an extendable grasping housing fixedly or removably attached to the outside of the catheter also reduces the chance of encountering a clogged lumen and interruption of suction. Further, the device gives medical personnel the availability to grasp and remove foreign bodies in the presence or absence of suction.

Examples of suitable materials include, without limitation, metal or metal compounds, polycarbonates, acrylics, polymers, plastics, or a combination thereof. It is contemplated that the device 100 is formed by additive manufacturing, injection molding, compression molding, extrusion, casting, blow molding, machining, heat forming, joining, bonding or combinations thereof.

In addition to the aspects described above, further improvements may be achieved by also including an auxiliary access port, through which various items may be administered, including one or more of a bougie instrument, oxygen, other gas, medications, etc., without removal of the suction catheter (e.g., a Yankauer suction catheter (also referred to herein generally and interchangeably as suction catheters, Yankauer devices, or Yankauers), either alone or as modified according to one or more of the embodiments described above). Emergency and medical personnel use Yankauers, or other suction devices (including those described in various embodiments above) to clear the mouth, pharynx and oropharyngeal cavity (airway) of gastric contents and fluids such as saliva and blood (viscous fluids). The proximal and distal ends of these devices are connected by a conduit capable of transporting fluids when the proximal end of the device is connected by a vacuum hose to a negative pressure device. Clearing the mouth and airway of fluids is done prior to intubating a patient.

The primary objective of intubation is to protect and maintain a patient's airway while administering anesthesia or in emergent circumstances, performing a life-saving intervention to restore oxygen and breathing to a patient suffering from respiratory failure. Before intubation can occur, a Yankauer or other suction device is used to clear the mouth of: saliva, blood, gastric fluids and debris. A laryngoscope is then used to shine light into the mouth and oropharyngeal cavity (airway) to move the tongue and appropriate anatomical structures out of the way in an effort to gain visual access of the patient's vocal cords. Visual access of the vocal cords is crucial since the endotracheal tube (ET tube) responsible for providing oxygen to the patient must first pass through the vocal cords and into the trachea. Even with the presence of a laryngoscope and ET tube in the confines of a small oral cavity, the suction device may be left in place during the intubation process. Once the anatomical target for ET tube insertion is obtained, suction may be necessary to remove additional blood or vomit that can visually obstruct the vocal cords and prevent intubation.

In approximately half of cases, insertion of the ET tube through the vocal cords and into the trachea is immensely difficult. Great care is taken to obtain successful insertion of the ET tube during the first try as subsequent attempts are less successful. The slightest anatomical movement or visual loss of the patient's vocal cords may further decrease the chance of successful intubation and increase the chances of patient injury or death.

Even in the absence of a contaminated airway, insertion of the ET tube frequently proves challenging in the delicate structures of the oropharyngeal cavity. Anatomical differences, muscle spasms and external factors often prevent the insertion of an ET tube from restoring oxygen and breathing to the patient. In these instances a small diameter, flexible, surgical instrument called a bougie is inserted through the opening of the vocal cords and into the trachea. The distal tip of the bougie is angled anteriorly to the trachea in order to provide audible and tactile feedback to the medical provider as the bougie is inserted into and pushed across the rings of the trachea. Once the bougie has reached the trachea, the ET tube is then placed over the bougie and serves as a guide to direct the ET tube through the opening of the vocal cords. After the ET tube has been correctly secured within the trachea, the bougie is withdrawn, additional instrumentation may be removed, and restoration of oxygen to the patient may begin.

The distal tips of typical suctioning devices designed for insertion into the oropharyngeal cavity are much smaller in comparison to laryngoscopes and are therefore more efficient at precisely supplying suction at targeted anatomical structures. Attempts have been made to utilize separate lumens to incorporate suction capabilities or bougie guides into laryngoscopes and ET tubes. However, these types of devices are not efficient at removing large volumes of viscous fluids at anatomical targets in a timely manner. In addition, the integration of bougie guidance and suction capabilities into non-dedicated oropharyngeal suction instruments prevents ideal anatomical placement of the device. For example, a primary purpose of a laryngoscope is to hold the tongue and soft palate structures laterally so visualization of the vocal cords may be obtained. Movement of the laryngoscope blade to a different anatomical site to provide suction requires the caregiver to release the anatomy the instrument blade was holding to provide visualization. Since a reduced number of airway instruments provide more anatomical landscape for medical personnel to work within, a modified Yankauer capable of providing suction through an auxiliary port is preferable.

In some cases, depending upon anatomy and the presence of viscus fluids, intubation may sometimes be obtained via direct visualization (i.e. in the absence of a laryngoscope). This is especially true in emergent care or outside-of-hospital circumstances. Even in cases of direct visualization and the absence of a laryngoscope, intubation-associated difficulties such as the potential need for suction and guidance of a flexible bougie through the anatomical target reduces the chances of successful intubation.

Traditional Yankauer and airway suction devices are inexpensive and commonly used in intubation procedures. They have remained relatively unchanged over the last 50 years and more advanced airway functions such as the addition of light sources, gas delivery, and the accommodation of bougie instruments have been reserved for more expensive, non-disposable instruments. There are currently no Yankauer instruments (airway suction devices) with an auxiliary access port that can accommodate, guide, and support insertion of a bougie through at least a portion of the lumen of the airway suction device without first disconnecting the suction source from the suction device. Furthermore, there remains a need for an auxiliary access port on a suction device that connects to an oxygen supply for the administration of oxygen through the lumen/bore of the airway suction device. Additionally, there remains a need for an auxiliary access port on a Yankauer instrument (suction catheter more generally) that allows for the delivery of medication through the lumen of an airway suction device.

The devices described herein overcome one or more of these noted deficiencies, and may be implemented with a traditional Yankauer suction device, or alternatively in combination with the other features of the present disclosure (including grasping device and/or auxiliary suction channels extending along an interior of the lumen, etc.).

It is an object of the present disclosure to provide a Yankauer suction device with an auxiliary access port through which a bougie instrument can be inserted into the interior bore of the suction device. The auxiliary access port and bore of the Yankauer suction device are sufficiently large enough to allow at least a portion of the distal end of the bougie instrument to exceed the distal end of the suction device.

In one aspect, the device comprises a substantially hollow suctioning tube coupled to an elongate grip or handle. The proximal end of the device is attached to a vacuum hose and negative pressure source capable of transporting viscous fluids through the distal end of the device through the proximal end of the handle. There is at least one central bore of the Yankauer in fluid communication with the distal and proximal ends of the suction device.

In another aspect, the distal end of elongate grip or handle may contain an integrated finger rest to increase ergonomics and provide greater operational control of the device. The proximal end of the handle comprises a vacuum attachment port with compression rings configured to receive and seal to the interior of a vacuum hose. The distal end of the Yankauer device includes at least one hole in fluid communication with the interior bore of the instrument.

In yet another aspect, the distal end of the Yankauer device includes a bulbous suction tip comprising multiple holes in fluid communication to the interior bore of the suction device to facilitate removal of viscous fluids.

In yet a further aspect, the auxiliary access port lies between the distal and proximal ends of the Yankauer suction device.

In an embodiment, the auxiliary access port is in fluid communication with the interior bore of the Yankauer device. While not in use, the lateral end of the auxiliary access port may be closed with any number of different caps or plugs to prevent loss of vacuum.

In another embodiment, the auxiliary access port may not be in fluid communication with the interior bore of the Yankauer device. In one instance the interior lumen of the auxiliary access port may be sealed with a septum, polycarbonate, or other material capable of preventing loss of vacuum while the auxiliary port is not in use (e.g., a sealing membrane). Piercing the septum within the auxiliary access port with the end of a bougie or other instrument begins fluid communication between the auxiliary access port and the internal bore of the suction device. Piercing the septum also allows the bougie to be further inserted through the interior bore of the suction device.

In yet another embodiment, the lateral end of the auxiliary access port may have male or female threads or one of any other type of connectors that allow for the connection of hoses or devices for the delivery of oxygen, gas, or medication, etc.

Further aspects include a method of inserting a bougie during an intubation procedure comprising: Removing a cap or plug from the distal end of the auxiliary access port, Inserting a bougie instrument into an auxiliary access port of a Yankauer suction device, Pushing the bougie through the bore of the suction device until the distal end of the bougie exceeds the distal end of Yankauer device. This method may further include utilizing suction through the bore of the Yankauer device before, during, or after introduction of the bougie instrument into the oropharyngeal cavity.

Particular embodiments of the present invention described in this document include numerous advantages. First, some embodiments of the auxiliary access port described herein allow the bougie to be easily guided to its anatomical target. It is known by individuals familiar with the art that anatomical targeting of the bougie may be difficult due to the instrument's flexibility, long length, and small diameter. Inserting the bougie through an auxiliary access port on a Yankauer device increases the trajectory accuracy of bougie insertion and decreases the application time.

Second, some embodiments of the present invention allow the bougie instrument to be inserted through the auxiliary access port of the suction device without first disconnecting the suction source from the proximal end of the suction device.

Third, in some embodiments of the present invention, the administration of oxygen, gas, and medications can be inserted through the auxiliary access port without removal of the Yankauer device. Although much larger and expensive laryngoscopes have employed separate lumens to increase the functionality of the instrument, their limitation is that the larger internal diameter of the Yankauer device provides for greater vacuum, gas movement, and targeting of a bougie. These features have been absent in inexpensive, disposable Yankauer devices.

For the purpose of clarification and described herein, Yankauer, suction device, and suction catheter may be used interchangeably and refer to oral suctioning instruments designed to be used by medical personnel in the mouth or oropharyngeal cavity. Moreover, mouth, airway, and oropharyngeal cavity may be used interchangeably and refer to anatomical cavities and structures between the inferior aspect of the soft and hard palates and extending to the superior aspect of the vocal cords. Additionally, distal end refers to the end of an instrument farthest away from the user and closest to the patient while proximal refers to the end closest to the user and farthest from the patient. Optionally, the proximal end may refer to the end of the device with the handle while the distal end may refer to the end of the device with the suction tip.

The present disclosure is directed to an improved Yankauer suction device by adding an auxiliary access port to the suction device. The auxiliary access port lies between the proximal and distal ends of the Yankauer device. For example, the auxiliary access port may be located closer to the proximal end of the Yankauer device, such as in proximity to a handle of the device, or formed/included as part of the handle itself. The auxiliary access port allows insertion of a bougie instrument (or other instruments, medications, fluids, etc.) through the bore of the Yankauer device and into the patient's airway without disconnection of the suction source from the suction instrument.

The improved Yankauer instrument increases the effectiveness of intubation by providing access and insertion of a bougie instrument through the bore of a suction device and into an airway without disconnection of the suction device from the suction source. Furthermore, during intubation the vocal cords are perhaps the most important anatomical structure that requires removal of viscus fluids and debris via suction as fluid that passes through the vocal cords may be aspirated into a patient's lungs. Having one instrument bore in immediate proximity of the vocal cords allows a single instrument to both guide the bougie to its anatomical target as well as suction viscous fluids away from the vocal cords, in a manner that other devices such as laryngoscopes are unable to achieve due to size and configuration, etc.

In addition to providing the benefits of providing suction and bougie placement through a Yankauer, the auxiliary access port allows for oxygen or medication to be delivered to the appropriate anatomical target without disconnection of the vacuum tube from the proximal end of the suction device.

The embodiments described herein provide medical personnel the ability to add multiple useful features to a common and inexpensive suction device that are normally only found on larger, more expensive instruments.

Turning now to FIG. 9, there is shown a Yankauer with an auxiliary access port 900 constructed in accordance with the principles of the present disclosure. As is illustrated in the front perspective view of FIG. 9, the Yankauer 900 has a proximal end 902 and a distal end 904. A handle section 906 comprises an elongated handle with a hollow suction port 908 at its proximal end. The exterior of the suction port 908 has a set of compression fitting rings 910 configured to attach to a vacuum hose and negative pressure source. An auxiliary access port 912 in integrated posteriorly into the proximal end of the handle 906. A hollow suction tube 914 extends from the distal end of the handle 906 and terminates into a suction tip 918. Further, the hollow suction tube 914 is made of a curved suction tube (more generally, the Yankauer device 900 is made of a curved structure, with a radius of curvature sufficient to navigate the oropharyngeal cavity of a patient.

As is illustrated in FIG. 10, the sectional view of the Yankauer device 1000 illustrates the connection between the auxiliary access port 1012 and the longitudinal bore 1020 that runs between the distal suction tip 1018 and proximal hollow suction port 1008. The suction tip 1018, elongated suction tube 1014, handle section 1006, auxiliary access port 1012 and hollow suction port 1008 are in fluid communication. An auxiliary access cap 1016 contains female threads and is removably attached to the distal end of the male threads on the auxiliary access port 1012. When the cap 1016 is secured to the auxiliary access port 1012, the distal end of the bore of the auxiliary access port 1012 is sealed.

Figure 11D:
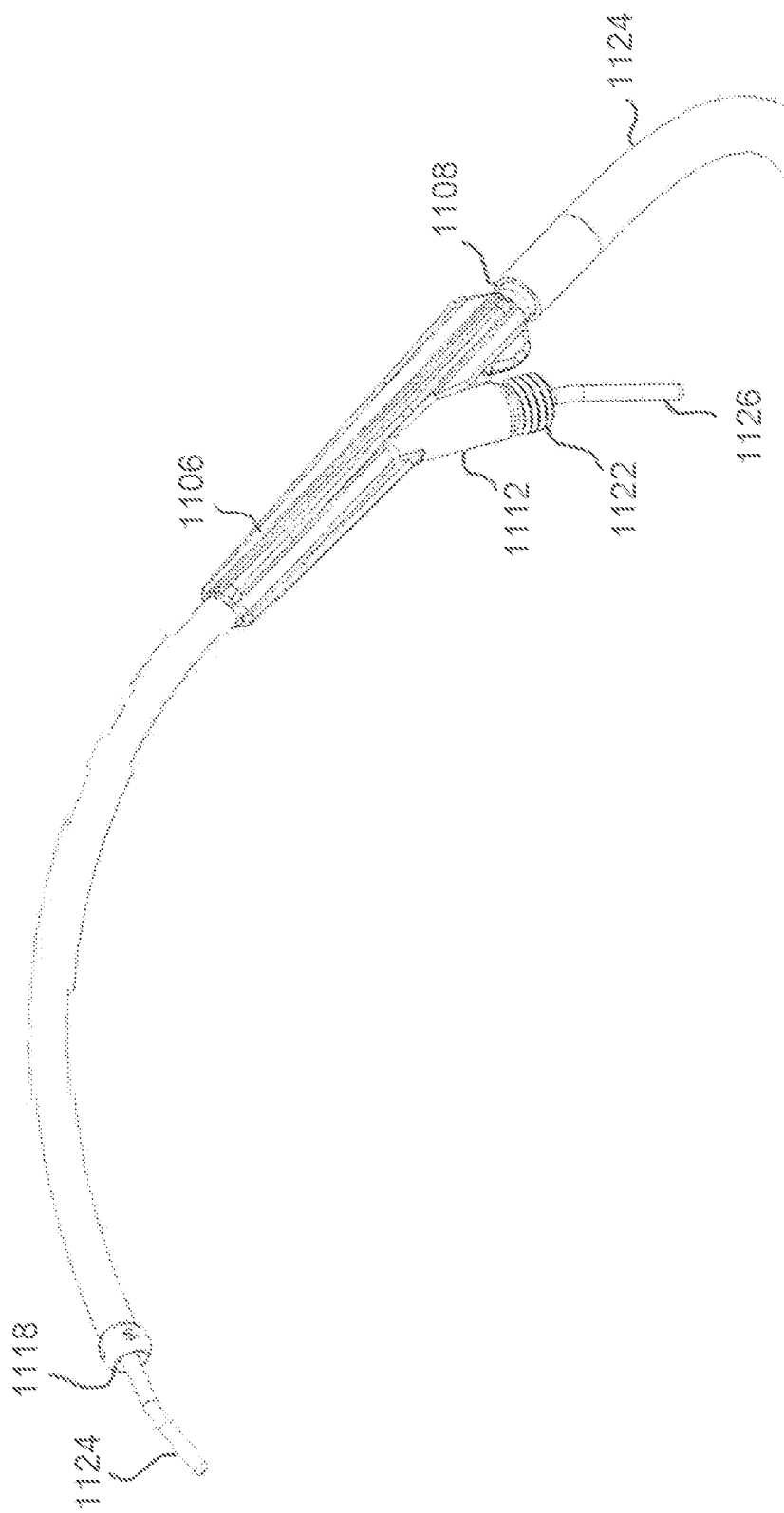

FIGS. 11A, 11B, 11C and 11D are partial side views of the present invention that illustrate the movement, position and insertion of the bougie instrument 1126 in relation to the auxiliary access port 1112 and handle section 1106. A vacuum hose 1124 of FIG. 11A is connected to the compression fitting rings 1110 of the hollow suction port 1108. The auxiliary access port 1112 is integrally connected to the handle section 106. The auxiliary access cap 1116 is removably attached to threads 1122 on the distal end of the auxiliary access port 1112. As depicted in FIG. 11B, the auxiliary access cap 1116 is removed from the threads 1122 of the distal end of the auxiliary access port 1112, the distal end of a bougie 1126 is inserted into the bore 1120 of the auxiliary access port 1112 and pushed distally through the hollow handle section 1106 and bore 1120 until the distal end of the bougie 1126 exceeds the distal end of the Yankauer device 900.

FIG. 11C depicts an angled tip of the bougie 1126 inserted through the auxiliary access port 1112 and through the handle section 1106 of the Yankauer device 900. FIG. 11C also depicts the vacuum hose 1124 removably attached to the hollow suction port 1108 of the proximal end of the Yankauer device 900.

Figure 12:
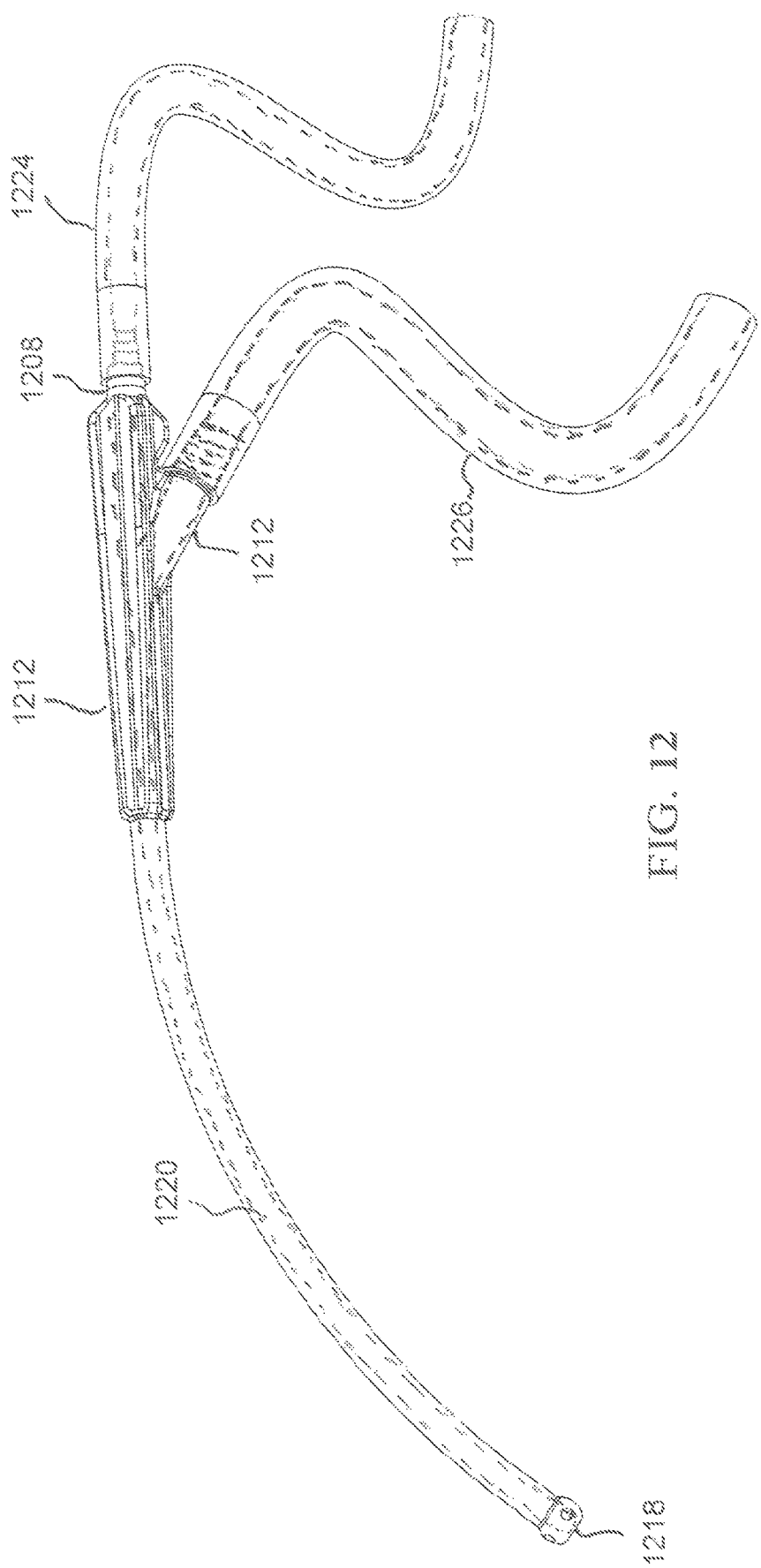
FIG. 12 illustrates a front perspective view of an oxygen hose connected to the Yankauer device of FIG. 9.

FIG. 12 illustrates an oxygen hose 1226 removably attached to the auxiliary access port 1212. Without disconnection of the vacuum hose 1224, oxygen may be pushed through the oxygen hose 1226, auxiliary access port 1212, bore 1220 and exit through the suction tip 1218 located at the distal end of the Yankauer 900.

An exemplary dimension of the Yankauer is 5 to 50 cm. in length and the internal diameter of the bore may be one to ten millimeters. In some examples, the inside diameter at the suction tip may be smaller than the inside diameter at the proximal end of the handle. Optionally, the inside diameter of the bore can remain constant. However, the preferences of medical personnel, patient size and circumstance ultimately determine the dimensions of the device.

This disclosure describes a novel auxiliary access port on the Yankauer device 900. Advantages of this configuration include, without limitation, a Yankauer device which is specifically designed to enter the oropharyngeal cavity and provide medical personnel the ability to evacuate viscous fluids and insert a bougie through an auxiliary access port into the bore of a Yankauer without disconnecting the suction hose from the Yankauer device. Additionally, incorporating an auxiliary access port onto a Yankauer device also provides better anatomical targeting for the bougie while providing circumferential suction around the distal end of the bougie tip if needed. Furthermore, the improved device also allows for the targeted administration of oxygen into the airway.

Examples of suitable materials include, without limitation, polycarbonates, polycarbonates, acrylics, polymers, plastics, or a combination thereof. It is contemplated that the Yankauer device 900 is formed by injection molding, compression molding, extrusion, casting, blow molding, machining, heat forming, joining, bonding or combinations thereof.

What is claimed is:

1. A suction catheter, comprising:
   an elongated suction tube having a lumen extending from a proximal end of the elongated suction tube to a distal end of the elongated suction tube, the distal end including a suction tip comprising at least two sets of pegs and the suction tube further comprising a radius of curvature between the proximal end and the distal end;
   a grasping housing slidably disposed around at least a portion of the elongated suction tube and the suction tip, comprising an upper grasping arm, a lower grasping arm, and a grasping tip formed from an upper distal end of the upper grasping arm and a lower distal end of the lower grasping arm, the grasping housing further comprising a plurality of slot ramps on the upper and lower grasping arms configured to engage with the at least two sets of pegs of the elongated suction tube,
   wherein the grasping housing is configured to extend from a first configuration to a second configuration, the first configuration comprising the grasping tip being situated in proximity to the suction tip in a closed configuration with the plurality of slot ramps engaging the at least two sets of pegs in a first slot ramp location, and the second configuration comprising the grasping tip extended a first distance distally from the suction tip in an open configuration with the plurality of slot ramps engaging the at least two sets of pegs in a second slot ramp location,
   wherein the grasping housing is further configured to extend from the second configuration to a third configuration, the third configuration comprising the grasping tip extended a second distance distally from the suction tip in a closed configuration with the plurality of slots ramps engaging the at least two sets of pegs in a third slot ramp location, the second distance being greater than the first distance; and
   an auxiliary access port located on the suction catheter between the proximal end and the distal end of the suction tube, the auxiliary access port comprising an opening and a hollow bore in fluid communication between the opening and the lumen of the suction tube, wherein the auxiliary access port is sized to receive an instrument through the opening and hollow bore and into the lumen, and a distal opening of the lumen is sized to receive the instrument extended through the distal opening.

2. The suction catheter of claim 1, wherein the suction tip of the elongated suction tube is sized to rest adjacent to a vocal cord of a patient.

3. The suction catheter of claim 1, wherein the auxiliary access port further comprises:
   a sealing membrane within the hollow bore that seals a remaining portion of the hollow bore that remains in fluid communication with the lumen of the elongated suction tube, wherein the sealing membrane is configured to be pierced by the instrument to allow the instrument to extend through the remaining portion of the hollow bore and the lumen.

4. The suction catheter of claim 1, wherein the instrument comprises a bougie instrument.

5. The suction catheter of claim 1, wherein the instrument comprises at least one of a source of oxygen, a source of medication, or a bougie instrument.

6. The suction catheter of claim 1, further comprising:
   a bulbous suction tip at the distal end of the elongated suction tube, the bulbous suction tip comprising a plurality of holes in fluid communication with the lumen.

7. The suction catheter of claim 1, wherein the proximal end of the elongated suction tube is coupled to a negative pressure source to provide suction via the lumen while the instrument is extended from the hollow bore of the auxiliary access port through the lumen.

8. A catheter device, comprising:
   an elongated suction catheter having a lumen extending from a proximal end of the elongated suction catheter to a distal end of the suction catheter, the distal end comprising a suction tip including at least two sets of pegs;
   an auxiliary access port located on the suction catheter between the proximal end and the distal, the auxiliary access port comprising an opening and a hollow bore in fluid communication between the opening and the lumen, the auxiliary access port being sized to receive an instrument through the opening and hollow bore and into the lumen; and
   a grasping housing slidably disposed around at least a portion of the elongated suction catheter and the suction tip, comprising a first grasping arm and a second grasping arm disposed around first and second respective portions of an exterior of the elongated suction catheter at the suction tip, and a grasping tip formed from a first distal end of the first grasping arm and a second distal end of the second grasping arm, the grasping housing further comprising a plurality of slot ramps on the first and second grasping arms configured to engage with the at least two sets of pegs of the elongated suction catheter,
   wherein the grasping housing is configured to extend from a first configuration to a second configuration, the first configuration comprising the grasping tip being situated in proximity to the suction tip in a closed configuration with the plurality of slot ramps engaging the at least two sets of pegs in a first slot ramp location, and the second configuration comprising the grasping tip extended a first distance distally from the suction tip in an open configuration with the plurality of slot ramps engaging the at least two sets of pegs in a second slot ramp location, and wherein the grasping housing is further configured to extend from the second configuration to a third configuration, the third configuration comprising the grasping tip extended a second distance distally from the suction tip in a closed configuration with the plurality of slots ramps engaging the at least two sets of pegs in a third slot ramp location, the second distance being greater than the first distance.

9. The catheter device of claim 8, wherein the suction tip and grasping tip are sized to reset adjacent to a vocal cord of a patient.

10. The catheter device of claim 8, wherein the auxiliary access port further comprises:

a sealing membrane within the hollow bore that seals a remaining portion of the hollow bore that remains in fluid communication with the lumen, wherein the sealing membrane is configured to be pierced by the instrument to allow the instrument to extend through the remaining portion of the hollow bore and the lumen.

11. The catheter device of claim 8, wherein the instrument comprises at least one of a source of oxygen, a source of medication, or a bougie instrument.

12. The catheter device of claim 8, wherein the elongated suction catheter further comprises a radius of curvature between the proximal end and the distal end.

13. The catheter device of claim 8, wherein the elongated suction catheter further comprises:

a plurality of auxiliary suction channels fluidly connected to the lumen of the elongated suction catheter extending from the suction tip to the proximal end.

* * * * *